(12) United States Patent
Manetta et al.

(10) Patent No.: US 8,239,780 B2
(45) Date of Patent: Aug. 7, 2012

(54) SYSTEM AND USER INTERFACE SUPPORTING TREND INDICATIVE DISPLAY OF PATIENT MEDICAL PARAMETERS

(75) Inventors: Amy M. Manetta, North Billerica, MA (US); Jolyn Rutledge, Amesbury, MA (US); Judith Shaffer, Orchard Park, NY (US)

(73) Assignee: Draeger Medical Systems, Inc., Andover, MA (US)

( * ) Notice: Subject to any disclaimer, the term of this patent is extended or adjusted under 35 U.S.C. 154(b) by 3244 days.

(21) Appl. No.: 10/359,673

(22) Filed: Feb. 6, 2003

(65) Prior Publication Data

US 2003/0200117 A1  Oct. 23, 2003

Related U.S. Application Data

(60) Provisional application No. 60/374,908, filed on Apr. 23, 2002.

(51) Int. Cl.
*A61B 5/05* (2006.01)
*A61B 5/044* (2006.01)
*G06Q 50/00* (2006.01)
*G06F 9/00* (2006.01)

(52) U.S. Cl. ............. 715/764; 600/301; 600/523; 705/2

(58) Field of Classification Search .................. 600/301, 600/523; 715/764; 705/2
See application file for complete search history.

(56) References Cited

U.S. PATENT DOCUMENTS

| | | | |
|---|---|---|---|
| 4,878,175 A * | 10/1989 | Norden-Paul et al. ............ | 705/2 |
| 5,253,362 A | 10/1993 | Nolan et al. .................. | 395/600 |
| 5,447,164 A | 9/1995 | Shaya et al. .................. | 128/710 |
| 5,682,526 A | 10/1997 | Smokoff et al. ............... | 395/615 |
| 5,772,585 A | 6/1998 | Lavin et al. ................... | 600/300 |

(Continued)

FOREIGN PATENT DOCUMENTS

| | | |
|---|---|---|
| WO | WO 94/13198 | 6/1994 |
| WO | WO 98/59487 | 12/1998 |
| WO | WO 01/88825 | 11/2001 |

OTHER PUBLICATIONS

Chelewski, Paula; Designing a patient-care 24-hour flowsheet; Apr. 1998; Nursing Management; Chicago (0744-6314) vol. 29,Iss.4;p. 37.*

(Continued)

*Primary Examiner* — Jordany Nunez
(74) *Attorney, Agent, or Firm* — Jack Schwartz & Associates, PLLC

(57) ABSTRACT

A user interface system provides patient medical parameter data for trend indicative display covering a time period comprising user selectable acquisition time intervals. An acquisition processor acquires, from a patient monitoring device, data representing a patient parameter comprising a plurality of data values at a corresponding plurality of different times within multiple user selectable patient parameter acquisition intervals of a time period. A generator generates data representing a first image showing a trend indicative display of the patient parameter covering a time period comprising user selectable acquisition time intervals and including a first number of data points in an individual acquisition time interval. The generator generates data representing an image window comprising an expansion of the individual acquisition time interval and including a second number of data points greater than the first number, in response to user command. The generator updates the individual acquisition time interval of the first image with at least one data point selected from the expanded individual acquisition time interval window to replace the first number of data points, in response to user command.

19 Claims, 9 Drawing Sheets

U.S. PATENT DOCUMENTS

| | | | | |
|---|---|---|---|---|
| 5,832,450 | A | 11/1998 | Myers et al. | 705/3 |
| 5,920,317 | A | 7/1999 | McDonald | 345/356 |
| 5,950,214 | A | 9/1999 | Rivette et al. | 707/512 |
| 6,026,363 | A | 2/2000 | Shepard | 705/3 |
| 6,055,506 | A | 4/2000 | Frasca, Jr. | 705/3 |
| 6,067,523 | A | 5/2000 | Bair et al. | 705/3 |
| 6,125,350 | A | 9/2000 | Dirbas | 705/2 |
| 6,155,974 | A | 12/2000 | Fish | 600/300 |
| 6,188,407 | B1 | 2/2001 | Smith et al. | 345/353 |
| 6,262,728 | B1 * | 7/2001 | Alexander | 345/440.1 |
| 7,006,862 | B2 * | 2/2006 | Kaufman et al. | 600/523 |

OTHER PUBLICATIONS

Solar Lab Access System General Information QS Workstation General Information.

HP M2000A Patient Documentation Center Metavision.

Tour Metavision Tour Workflow Support Solar Unit Manager System General Information HP Carevue Clinical Information System Tour Analysis HPM2000A Central Data Management for the Critical Care Environment Agilent Technologies Viridia Documentation Center HP Carevue Data Reporting Solution.

* cited by examiner

SYSTEM AND USER INTERFACE SUPPORTING TREND INDICATIVE DISPLAY OF PATIENT MEDICAL PARAMETERS

This is a non-provisional application of provisional application Ser. No. 60/374,908 by A. M. Manetta et al. filed Apr. 23, 2002.

FIELD OF THE INVENTION

This invention is related to the processing and displaying of medical information, and more particularly to processing and displaying of patient medical data including patient vital signs in a network environment.

BACKGROUND OF THE INVENTION

Patient medical parameter data is acquired, collated, stored and displayed for use in providing patient clinical care in hospitals, clinics, and other healthcare delivery settings. Patient medical parameter data may include vital signs ventilator information, infusion pump data associated with fluid delivery and other data. Such patient medical parameter data is typically displayed on a patient monitoring device screen in a trend indicative chart with a time axis. This type of chart is commonly termed a Flowsheet. A patient monitoring device is usually located at a patient bedside or nursing station in a hospital ward or in an intensive care, surgical or other location and may be connected to a network such as the Internet, a LAN, a WAN or an intra-net for acquiring patient parameter data from local sources (e.g., patient attached sensors) or remote sources (e.g., a remotely stored electronic patient record). The Flowsheet is an electronic chronological chart of patient information that substitutes for a paper vital sign Flowsheet.

It is desirable that Flowsheet generation systems enable a user to examine the actual data points displayed within a parameter acquisition interval and further enable a user to edit these data points to indicate the Flowsheet is truly representative of a patient condition. The known systems for generating a Flowsheet are limited in their capabilities. Specifically, known systems provide limited support for user examination, editing validation and selection of data points of a displayed Flowsheet. A system according to invention principles addresses these limitations and derivative problems.

SUMMARY OF THE INVENTION

A user interface system provides a Flowsheet with a zoom window function enabling user examination, validation, editing and selection of data points associated with particular parameter acquisition time intervals to improve accuracy of trend indicative patient parameter data for storage or display. A user interface system provides patient medical parameter data for trend indicative display covering a time period comprising user selectable acquisition time intervals. An acquisition processor acquires, from a patient monitoring device, data representing a patient parameter comprising a plurality of data values at a corresponding plurality of different times within multiple user selectable patient parameter acquisition intervals of a time period. A generator generates data representing a first image showing a trend indicative display of the patient parameter covering a time period comprising user selectable acquisition time intervals and including a first number of data points in an individual acquisition time interval. The generator generates data representing an image window comprising an expansion of the individual acquisition time interval and including a second number of data points greater than the first number, in response to user command. The generator updates the individual acquisition time interval of the first image with at least one data point selected from the expanded individual acquisition time interval window to replace the first number of data points, in response to user command.

DETAILED DESCRIPTION

Figure 1:
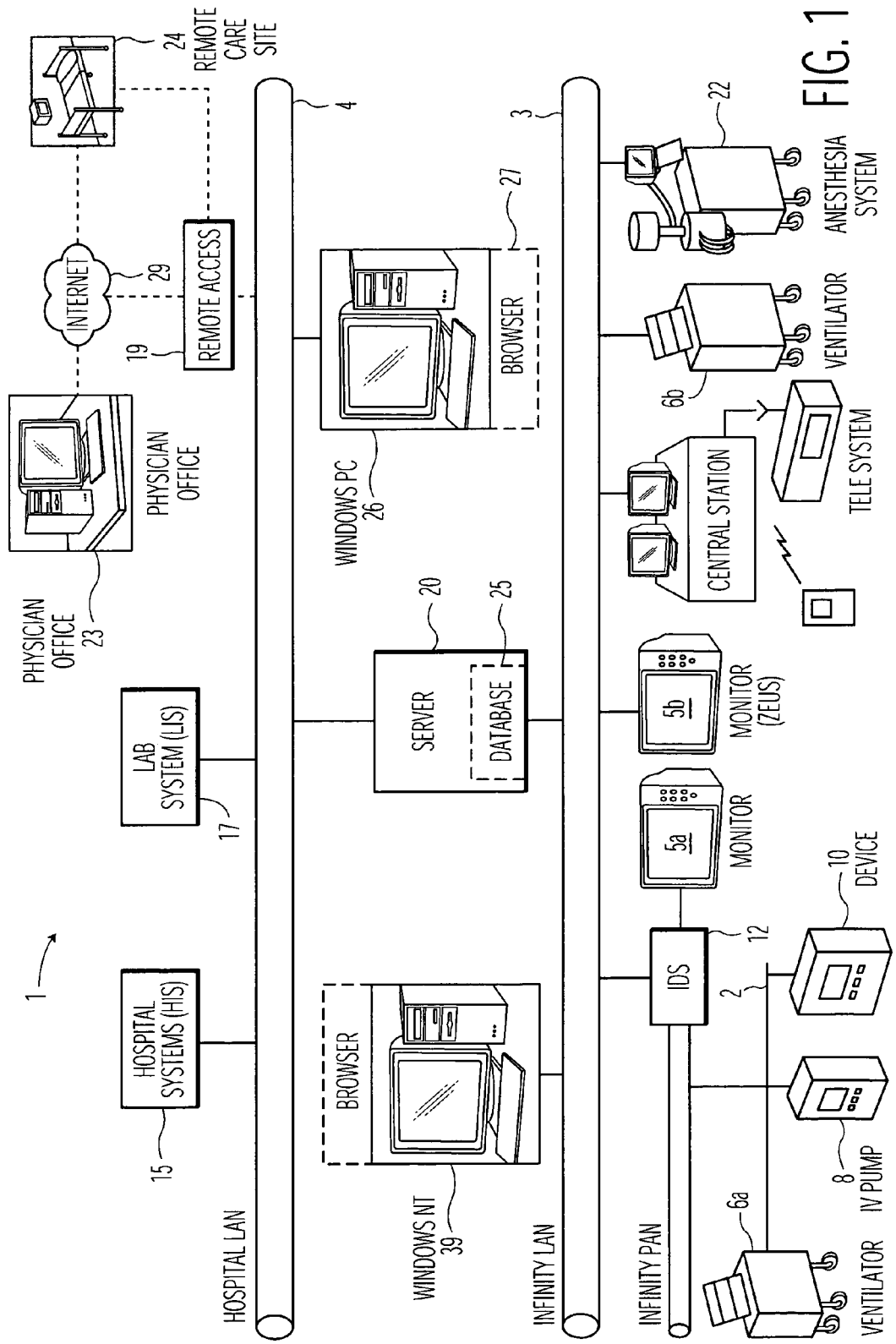
FIG. 1 is a block diagram of a communication network with various devices, according to the principles of the invention.

FIG. 1 is an exemplary block diagram of a communication network incorporating server 20 hosting an executable application providing a trend indicative user interface display of patient parameters (termed a Flowsheet) with a zoom window function enabling user examination, validation, editing and selection of data points associated with particular parameter acquisition time intervals. This user interface system advantageously facilitates improvement in accuracy of trend indicative patient parameter data for storage or display. In alternative embodiments, the executable application providing the user interface may be resident in another processing device in any part of the network shown in FIG. 1. The FIG. 1, communication network 1 is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown In FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a patient's room to administer care to a particular patient and to monitor the particular patient. Various medical devices may be connected via MIB 2; examples shown in FIG. 1 comprise a ventilator 6a, IV (Intravenous) Pump 8 or other medical equipment 10. MIB 2 is typically connected to a second level LAN network 3 through an Interface Docking Station (IDS) device 12, for interfacing to Ethernet-compatible LAN network 3. The LAN 3 may be for example, an Infinity LAN, marketed by Siemens Medical System. This higher-level LAN 3 is typically, though not necessarily, used by a particular department within a hospital, such as an intensive care department or surgery department, etc., depending on the size of the organization.

Although not shown in FIG. 1, more than one MIB may be connected to the second level LAN 3, so that more than one patient may be monitored or provided with care through LAN 3. In addition, medical devices may be connected directly to higher-level LAN 3. For example, as shown in FIG. 1, a ventilator 6b and an anesthesia system 22 are connected directly to LAN 3, without use of a MIB. Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 19 which provides remote, secured access from, for example, a remote doctor's office 23 or a remote care site 24, to the various systems and devices on network 1, through for example, Internet 29. Alternatively, a remote site may also access the remote access gateway 19 directly through, for example, a dial-up telephone port, ADSL, or other types of private connection. Remote access gateway 19 may also be part of server 20, to be described below, instead of standing alone, as well know in the art.

According to the principles of the present invention, an executable application (or multiple applications in another embodiment) resides on central server 20 on LAN 3 for gathering and processing data from the peripheral medical devices or facilities coupled to LAN 3 or hospital LAN 4, including laboratory results supplied via laboratory system 17 connected through an HL7 interface, for example. Additional medical parameter data including additional laboratory results acquired from any number of medical devices such as those shown in FIG. 1 may be obtained by server 20 using ASTM messaging, for example. The acquired medical parameters associated with a given patient, including laboratory test results, are acquired from the medical devices on network 1 for display and control on monitors 5a, 5b or PCs 26 and 39 or any other display hosting device at any level of the FIG. 1 network. One skilled in the art can readily recognize that server 20 may reside at any level of the hierarchy of network 1, since all the different levels of LANs (e.g., 3, or 4), as well as remote sites in FIG. 1 are interconnected. An example of server 20, is a Prometheus server, marketed by Siemens Medical System. The server may be hosted, for example, by a computer system that is capable of running Microsoft NT operating system.

The server 20 executable application provides a user interface trend indicative display of patient parameters (a Flowsheet) covering a time period comprising user selectable acquisition time intervals. A user selectable acquisition time interval represented by a column in the Flowsheet covers a time period (typically 3 minutes to 4 hours or another user selectable range) in which patient parameters are acquired. The server 20 executable application filters acquired patient parameter data to reduce the quantity of acquired patient parameter data to a manageable quantity suitable for display or storage. Specifically, the server 20 application filters acquired patient parameter data to provide one or more particular data points to represent a corresponding particular acquisition time interval in a patient parameter trend indicative display.

Patient parameter data acquired from patient attached equipment may be characterized as of continuous or discrete type. Continuous patient parameter data is periodically sampled and acquired at intervals typically of higher frequency than a displayed acquisition interval and discrete patient parameter data is acquired at non-periodic intervals (e.g., upon nurse measurement initiation) or at periodic intervals of relatively low frequency compared to continuous patient parameter data. The server 20 executable application automatically filters acquired continuous patient parameter data by selecting a patient parameter value that substantially occurs at (or reasonably near) the centre time of an individual acquisition time interval for display in a Flowsheet column representing an acquisition time interval. Specifically, the selected continuous patient parameter value is incorporated in an Internet compatible (web based) Flowsheet column representing the individual acquisition time interval. The server 20 executable application automatically filters discrete acquired patient parameter data by selecting a patient parameter value that occurs at a time closest to the centre time of an individual acquisition time interval for display in a Flowsheet column. Further, the server 20 executable application advantageously supports generation of a Cursor Tool and user interface image windows enabling a clinician (or other user) to examine, edit, validate or annotate filtered data points or to select alternative acquired patient parameter data points to represent Flowsheet column acquisition intervals (and to override automatically filtered data).

Figure 2:
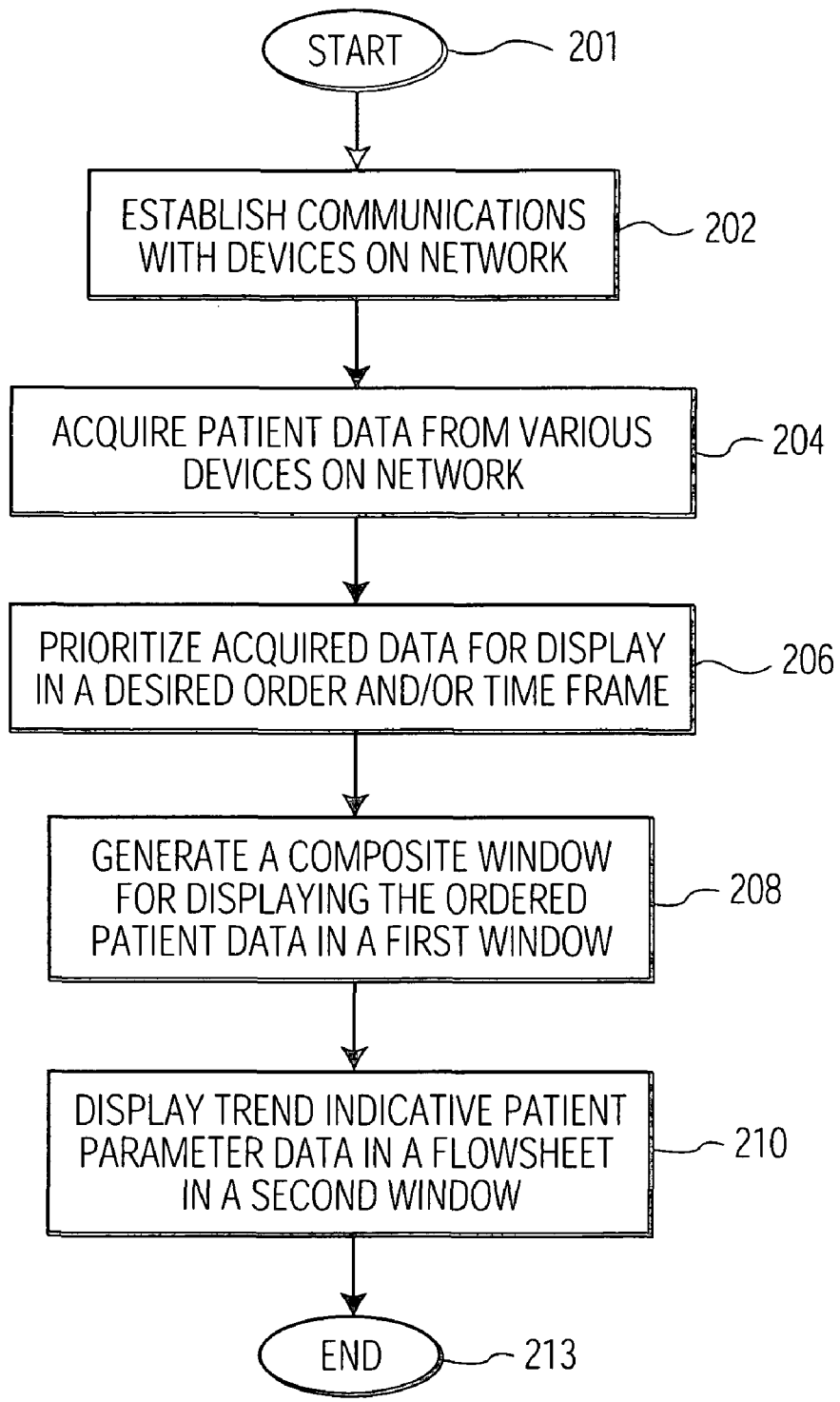
FIG. 2 represents a flowchart of a method for providing a user interface, according to the present invention.

FIG. 2 shows in flow chart form, functions that are performed by the server 20 executable application. The server 20 executable application establishes communication with devices on the network as shown in step 202 after the start at step 201. This is done, for example, by using IP protocol and the known IP device address for each device on the network 1 (FIG. 1), in conjunction with any higher application-layer protocols, as well known in the art. Once communication is established between server 20 and the other devices, the server 20 application in step 204 starts to acquire parameters that are being monitored, laboratory results and settings selected for the various devices. As previously mentioned, laboratory results may be obtained through an HL7 interface with LIS 17, or via ASTM or MIB point of care (POC) medical devices depicted in FIG. 1.

Medical data and laboratory results may be continuously, periodically or non-periodically acquired and correlated with a given patient for storage in relational data base 25 within server 20. Data base 25 may be of the type used for storing relational data such as the Microsoft SQL server. In addition, the server 20 application may obtain patient parameter data and patient data comprising medical laboratory results that are first entered and stored, for example, in laboratory system 17 of FIG. 1. Also, the server 20 application may acquire healthcare provider entered medical notes for display. At step 206, the server 20 application, in response to a user command, prioritizes and stores acquired patient data in server 20, in a desired order and/or time frame for display. The server 20 application generates a window for displaying trend indicative patient parameter data including vital signs, ventilator information, infusion pump data associated with fluid delivery and other data in a Flowsheet in steps 208 and 210, for example. The patient parameter data may be a blood pressure parameter, a ventilation parameter, a vital sign parameter, a blood oxygen concentration representative parameter or an infusion pump parameter associated with fluid delivery, for example. The server 20 application also generates a composite window for displaying concurrently, for example, a first window showing ordered patient data and a second window showing patient parameter data, medical laboratory results or user entered medical notes, in steps 208 and 210. The process of FIG. 2 ends at step 213

In one aspect of the present invention, a user may use a Microsoft Windows compatible PC 26 or Windows NT compatible PC 39 as shown in FIG. 1, or any other processing devices capable of running a menu generating program such as a web browser program (e.g., Microsoft Internet Explorer or Netscape Navigator, etc.) to view a Flowsheet, medical parameters and laboratory results information associated with a given patient. That is, a user may use a web browser on any processing device, as long as a communication connection can be made to server 20, to make request and view information acquired and stored in data base 25. This is advantageous, since a doctor may for example, gain access to a Flowsheet or laboratory test results from, for example, a remote physician's office 23, without having to access a dedicated terminal. Of course, a user can simply use a keyboard and/or a mouse or any other user interface devices to enter a user selection or request on a user computer, as is known in the art. Server 20 is therefore capable of collating and formatting medical data to be compatible with, for example, HTML (HyperText Mark-up Language) programming language for displaying data on a web browser. Server 20 is also responsive to, for example, HTTP (HyperText Transfer Protocol) commands originated from a user's web browser for making a request.

Figure 8:
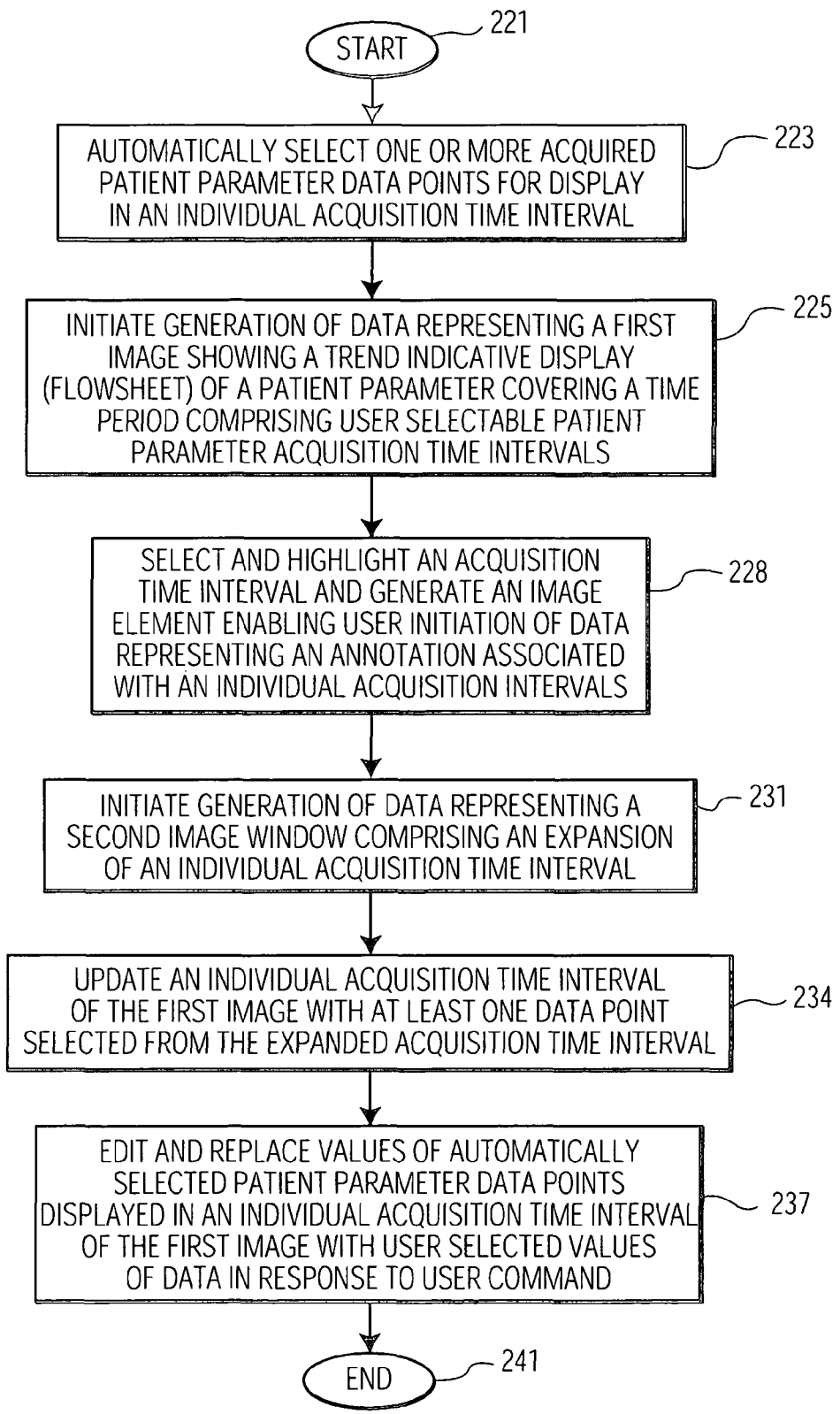
FIG. 8 is a flowchart of a method for providing a user interface, system for displaying patient medical information, according to the present invention.

FIG. 8 is a flowchart of a method for providing a user interface, system for displaying patient medical information. In step 223, following the start at step 221, the server 20 application automatically filters and selects one or more continuous or discrete data points (as previously explained), derived from the patient parameter data it previously acquired, for display in a Flowchart column representing an individual acquisition time interval. In step 225, the server 20 application initiates generation of data representing a first Flowchart image showing a trend indicative display of an acquired patient parameter covering a time period comprising user selectable acquisition time intervals as illustrated in FIG. 3.

Figure 3:
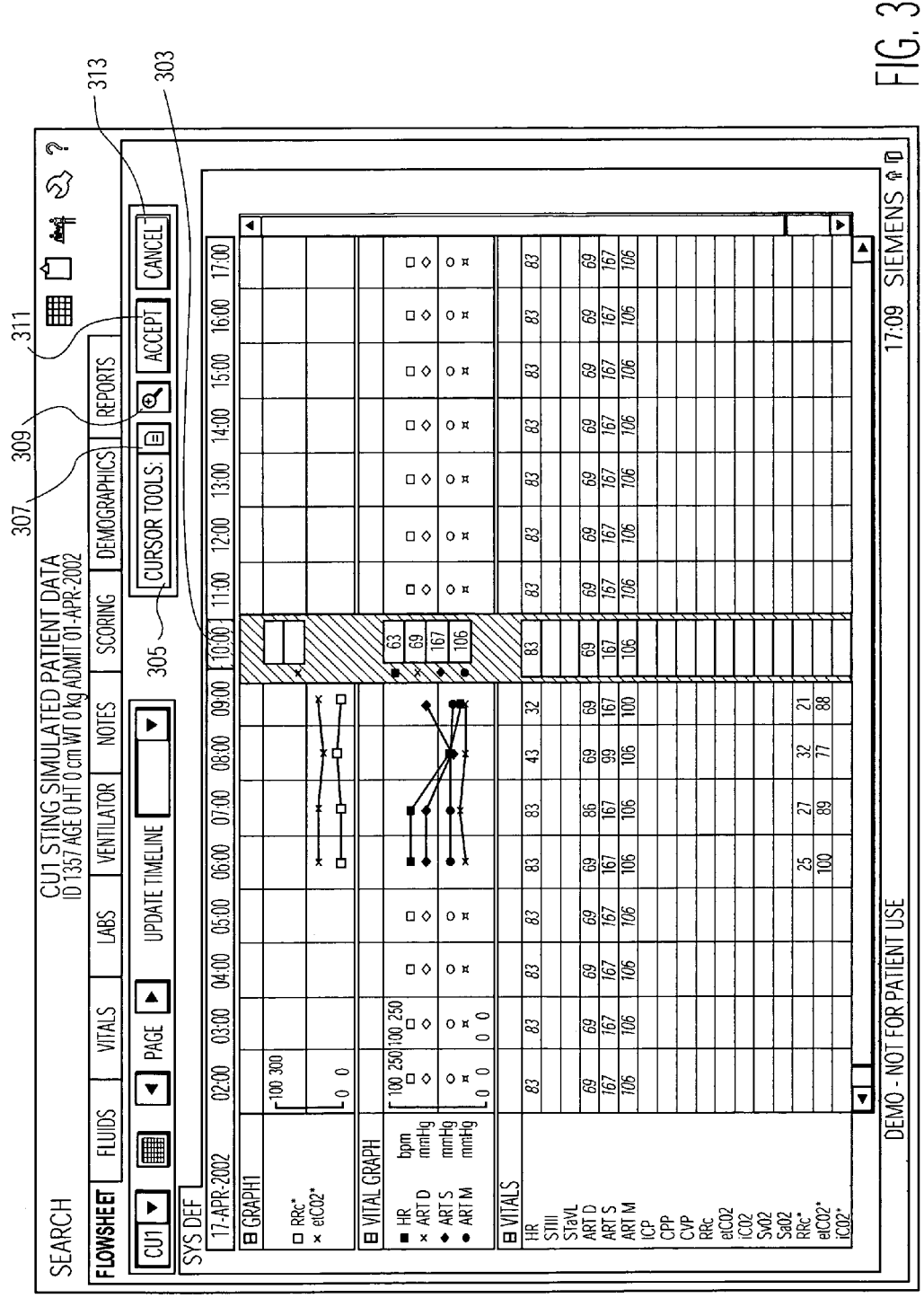
FIG. 3 shows a user interface display image supporting user editing of patient medical parameter data in a trend indicative display, according to the present invention.

The Flowsheet of FIG. 3 employs a Cursor Tool, which allows a user to edit, validate and annotate data in the electronic Flowsheet. In response to user selection of an individual acquisition time interval of a patient parameter such as the time interval indicated in column 303 of the FIG. 3 Flowsheet, a Cursor function of the server 20 application is initiated and a Cursor Tool is displayed within column 303 along with a Cursor tool control panel 305. Individual patient parameter acquistion time intervals are identified by a displayed time indicating the centre time of the acquistion time interval. The individual acquistion time interval indicated in column 303 has a centre time of 10:00 am, for example. The Cursor Tool function initiates generation of a display element (an edit box) supporting editing of patient parameter data in column 303. Similarly, the Cursor Tool function initiates generation of a displayed patient parameter edit box supporting user editing of patient parameter data in any column corresponding to any user selected acquisition time interval. Further, control panel 305 contains four user activatable buttons including an Annotate button 307, a Zoom button 309, an Accept button 311 and a Cancel button 313. In response to user selection of an acquistion time interval, the Cursor tool function of the server 20 application, in step 228 (FIG. 8), highlights an acquisition interval. The Cursor Tool function also generates an image element enabling initiation of generation of data representing an annotation associated with an individual acquisition time interval for incorporation in the Flowchart.

Figure 4:
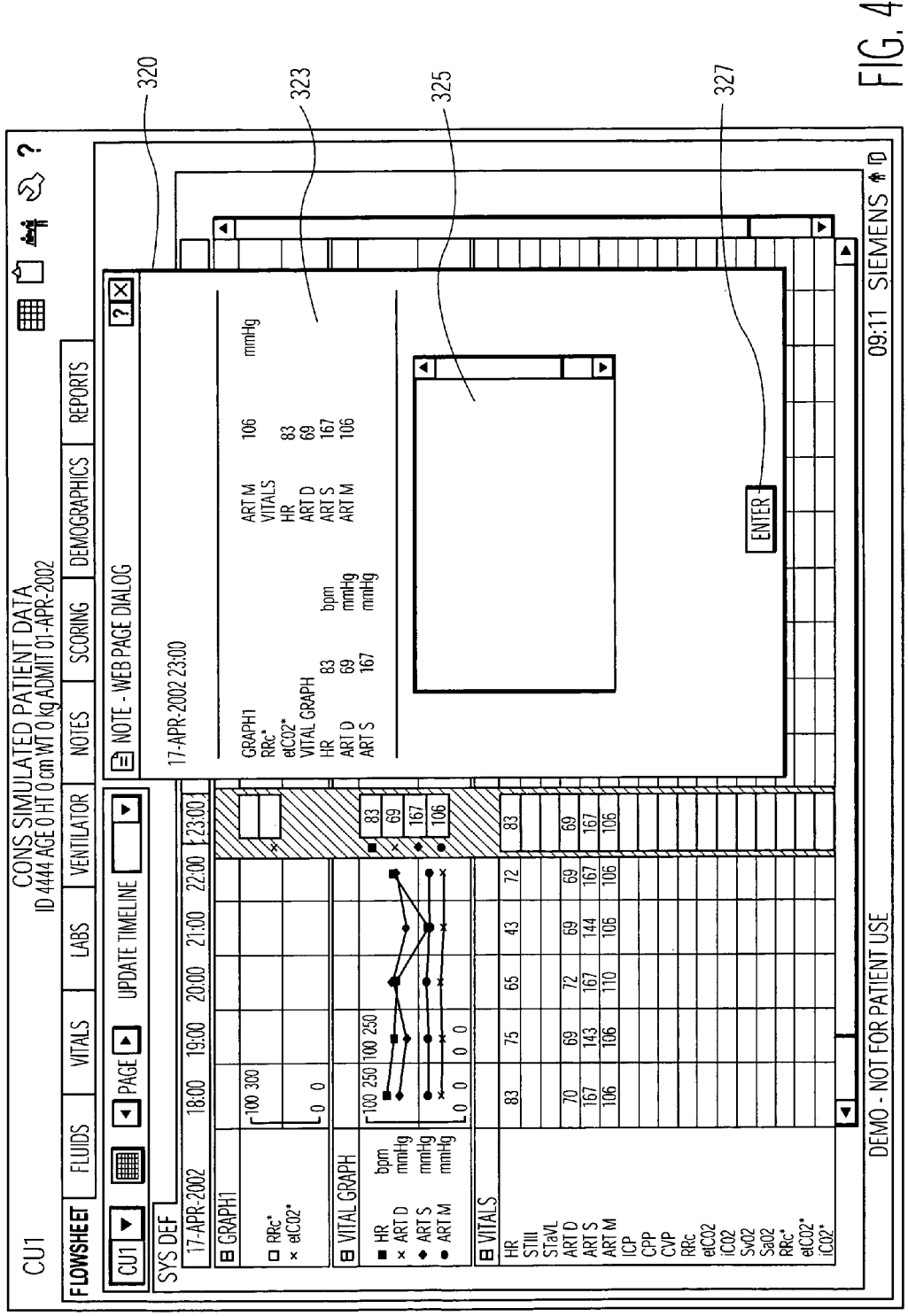
FIG. 4 shows a user interface display image supporting user annotation of patient medical parameter data in a trend indicative display, according to the present invention.

For this purpose, in response to user selection of Annotate button 307 (FIG. 3) in Control panel 305 a popup menu 320 is displayed as illustrated in FIG. 4. Popup menu 320 of the user interface display image of FIG. 4 enables a user to annotate patient medical parameter data in the Flowsheet. Further, popup menu 320 includes a table 323 containing the non-blank data in the selected (and Cursor Tool highlighted) patient parameter acquistion time interval of column 303. Text input window 325 enables a user to input an annotation associated with the selected acquistion interval of column 303. In response to user initiation of entry of an annotation (input in text box 325) via selection button 327, an annotation symbol is displayed at the top of column 303 (FIG. 3). This annotation symbol may be selected at any time to view the entered annotation.

Figure 5:
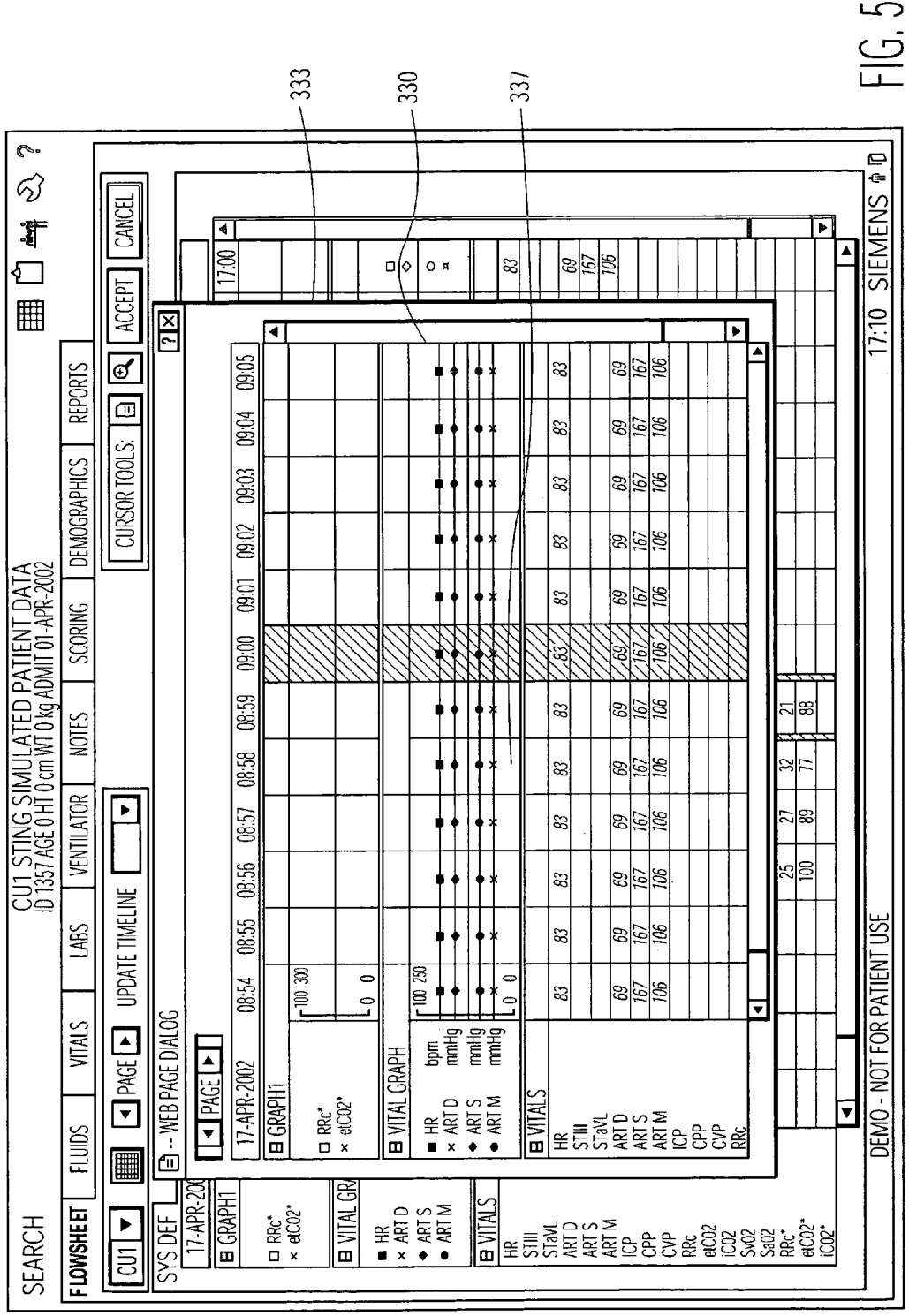
FIG. 5 shows a user interface display expansion (zoom) window comprising an expanded patient medical parameter acquisition time interval, according to the present invention.

Returning to the flowchart of FIG. 8, the server 20 application in step 231, initiates generation of data representing an image window comprising an expansion of the selected individual acquisition time interval in response to user selection of Zoom button 309 of control panel 305 (FIG. 3). FIG. 5 shows a user interface display expansion (zoom) window 330 comprising an expanded patient medical parameter acquisition time interval corresponding to an acquisition interval selected in the Flowsheet of FIG. 3 (encompassing the time period represented by expansion window 330). Column 333 in expansion window 330 is shaded to identify the expansion window column corresponding to a centre time of the selected acquisition time interval of FIG. 3 (an interval with a centre time of 09:00 am is indicated in the example of FIG. 5). Expansion window 330 shows a user a greater number of acquired patient parameter data points than the number of data points displayed in the corresponding acquisition time interval of FIG. 3. This is because expansion window 330 includes the acquired continuous (or discrete) patient parameter (raw) data that is automatically filtered and excluded by the server 20 executable application in step 223 (FIG. 8) from the acquisition time intervals of the Flowsheet of FIG. 3. Individual columns in expansion window 330 comprise 1 minute duration patient parameter acquisition time intervals (but in other embodiments may comprise other time periods). Expansion window 330 displays acquired patient parameter raw data covering a time period of 10 minutes before the selected column centre time to 10 minutes after the centre time. There are therefore 20 columns of patient parameter raw data available for display in this window by using horizontal image window navigation icons (using the displayed arrow buttons). Similarly, the user may also navigate and display the next or previous 20 minutes of data in expansion window 330.

Figure 6:
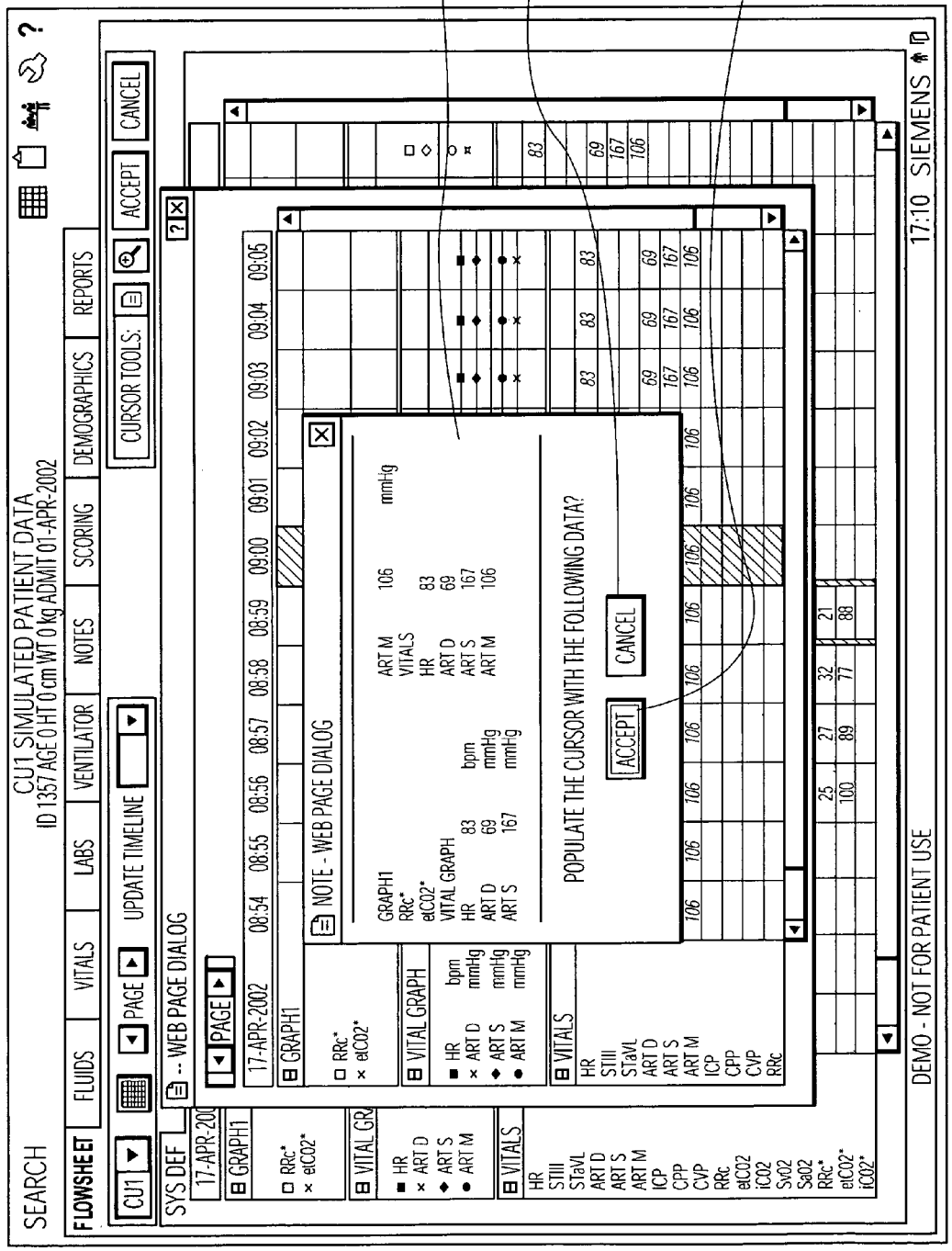
FIG. 6 shows a user interface display window supporting user selection and editing of patient medical parameter data in the expansion window of FIG. 5, according to the present invention.

In step 234 of FIG. 8 the user interface display image of FIG. 6 is employed to update an individual acquisition time interval of a first Flowsheet image (shown in FIG. 3) with at least one corresponding data point selected from expansion window 330. FIG. 6 shows a user interface display window incorporating popup menu 340 supporting user selection and editing of patient medical parameter data in the expansion window of FIG. 5. Popup Menu 340 is displayed in response to user selection of a column (e.g. column 337) within expansion window 330 of FIG. 5. A user employs popup menu 340 (FIG. 6) to replace an automatically filtered and selected data point currently representing a Flowsheet acquisition time interval with an alternative data point displayed in a column in expansion window 330 (FIG. 5) that a user determines more closely represents the true condition of the patient. In response to user selection of column 337 in expansion window 330 (FIG. 5), popup menu 340 of FIG. 6 is displayed containing the non-zero valued data of column 337. In response to a user data acceptance command (via icon 343), individual cells of the corresponding Flowsheet acquisition time interval column highlighted by the Cursor Tool (e.g. column 303 of FIG. 3), are populated with corresponding non-zero valued data of column 337 (FIG. 5) and popup menu 340 (FIG. 6) is removed. A user is able to inhibit update of column 303 using cancel icon 345 of menu.

In step 237 of FIG. 8, the Cursor Tool function of the executable application of server 20 enables editing and replacing values highlighted by the Cursor Tool (e.g., in column 303 of FIG. 3). The values highlighted by the Cursor Tool may be populated values previously selected using expansion window 330 of FIGS. 5 and 6, or values of automatically filtered and selected data points of the acquired patient parameter data. The user is able to employ the Cursor Tool function of the executable application of server 20 to further edit and replace these values in highlighted column 303 (FIG. 3) for example with user selected values of data, in response to user command. Following user selection and editing of data values in highlighted column 303, a user initiates acceptance or cancellation of edited data via Accept button 311 (FIG. 3) or Cancel button 313 of control panel 305. In response to user initiation of an acceptance command via button 311, the Cursor Control function highlighting and Cursor Tool format of column 303 as well as Control Panel 305 are removed and the current data in column 303 is replaced with the corresponding edited data for display in the FIG. 3 Flowsheet. Prior to replacing the data in column 303, the edited data is validated using predetermined reasonableness criteria including magnitude, range and polarity criteria. Further, the edited data in column 303 is marked as validated and column 303 cells, which are changed, are marked as edited. Non-Validated data in column 303 is displayed in Italics, validated data is displayed in normal text and edited data is displayed in bold, in the FIG. 3 Flowsheet. In response to user initiation of a cancellation command via button 313, the Cursor Control function highlighting and Cursor Tool format of column 303 as well as Control Panel 305 are removed and the current data in column 303 is left unaltered.

Figure 7:
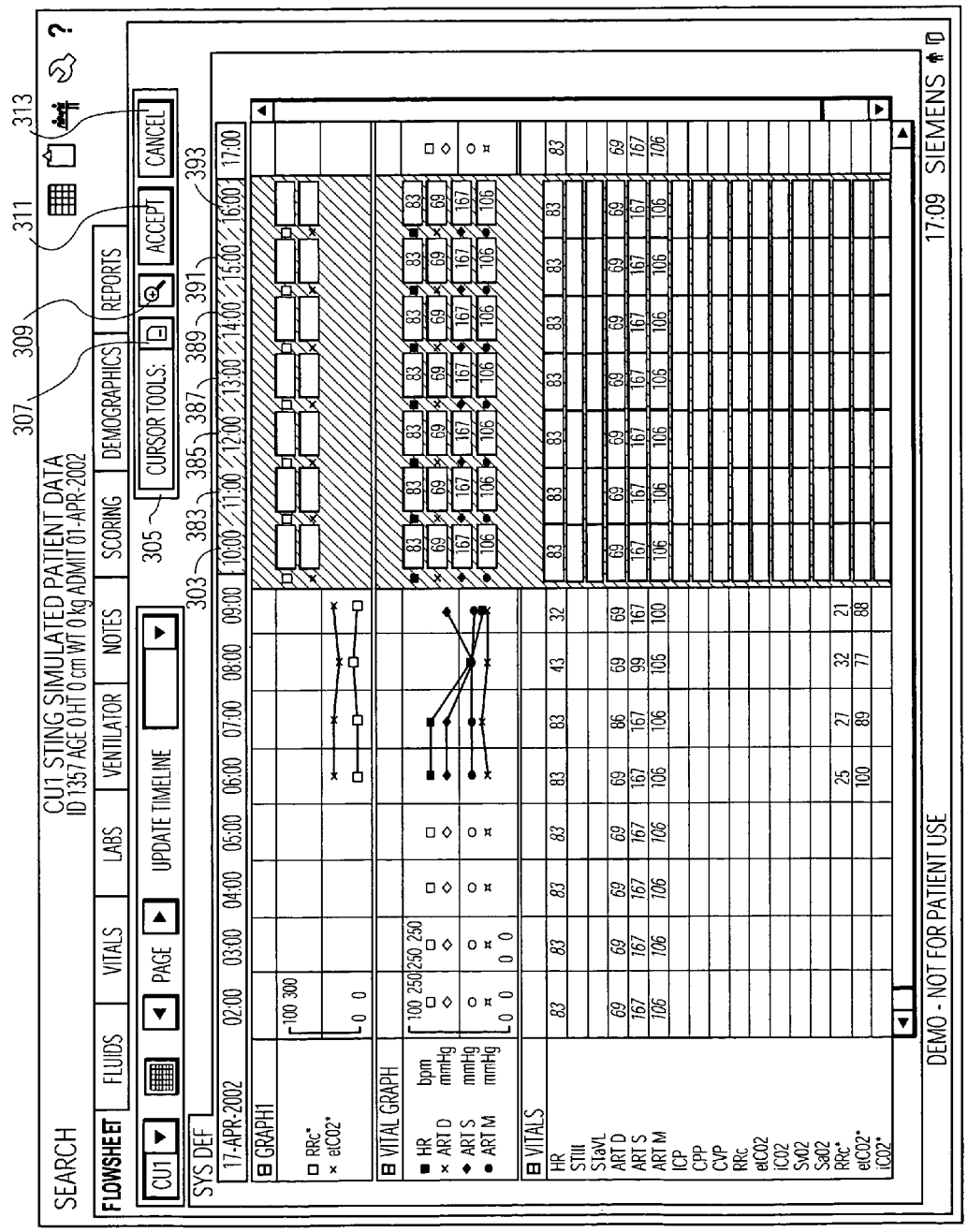
FIG. 7 shows the patient parameter editing user interface display image of FIG. 3 encompassing multiple acquisition time intervals of a trend indicative display, according to the present invention.

FIG. 7 shows the use of the Cursor Tool function with multiple acquisition time intervals of the FIG. 3 Flowsheet. The Cursor Tool function of the server 20 application is expanded in FIG. 7 to cover multiple columns (columns 303 and 383-393) of Flowsheet data. This is done by dragging either side of the Cursor Tool exhibited in column 303, for example, to cover the desired columns that a user wishes to edit/validate. Thereby, the user is able to select and edit data in the multiple columns covered by the Cursor Tool. Also, in response to user initiation of an acceptance command via button 311 (control panel 305), existing data in the selected multiple columns is replaced with corresponding edited data for display in the Flowsheet in a similar manner to that described in connection with FIG. 6. User activation of the acceptance command also initiates validation of the edited data against predetermined reasonableness criteria including magnitude, range and polarity criteria. The cancel function (initiated via button 313) also operates in a similar fashion to that described in connection with FIG. 6. The Annotate and Zoom functions (initiated via buttons 307 and 309) are restricted to operate with the Cursor Tool limited to occupy a single column width. The process of FIG. 8 terminates at step 241.

Figure 9:
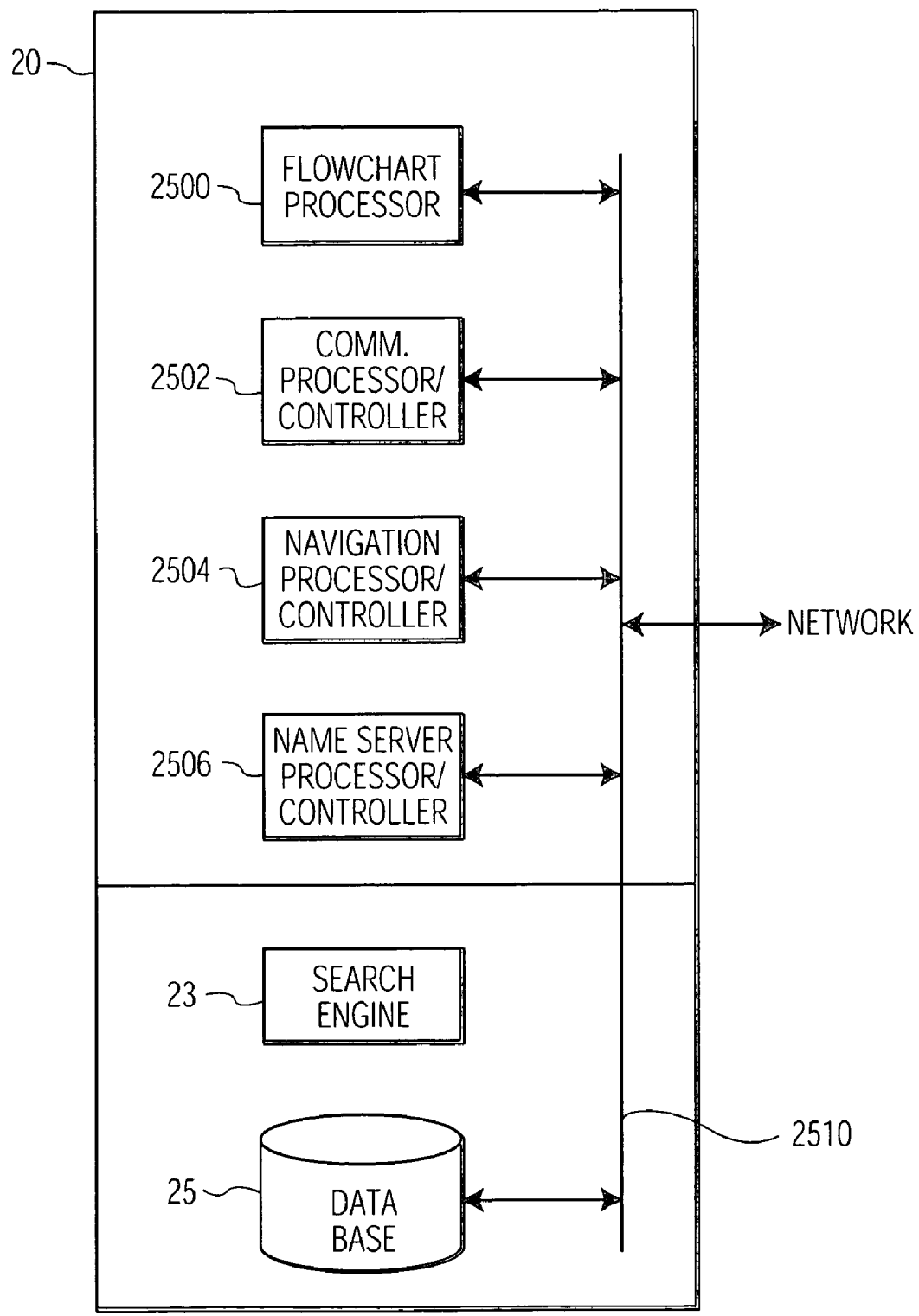
FIG. 9 is a block diagram of a server having functionality in accordance with the present invention.

FIG. 9 shows a block diagram of an exemplary embodiment of the server 20 which operates to manage, collate, search and update the data base 25 containing patient medical information. Program elements or processors operative to carry out instructions for performing the various functions described herein include an executable application 2500 for performing Flowchart related processing and communications processing module 2502 that acquires the patient data including the monitored parameters allocated to a given patient from the network and collates the information for storage in data base 25. Navigation collation processor 2504 operates in conjunction with the web browser and display generator software to collate and prioritize parameters for display to the user while navigating through various applications selected by a user through the user interface. Name server processor 2506 associates unique identifiers (IDs) with each node connected to the system network and with each patient in the system in order to track and update patient information throughout the system. Input/output data and control signals are used to communicate between the various processors as well as to interface with the data base 25 and search engine 23 and with the network via communication line 2510.

The Flowchart user interface display images, systems and processes presented in FIGS. 1-9 are not exclusive. Other Flowchart display images, systems and processes may be derived in accordance with the principles of the invention to accomplish the same objectives. Although this invention has been described with reference to particular embodiments, it is to be understood that the embodiments and variations shown and described herein are for illustration only and that various modifications may be implemented by those skilled in the art without departing from the scope of the invention. Flowchart user interface functions and Cursor Tool functions according to invention principles may be applied to any table which is composed of electronically filtered or selected data.

What is claimed is:

1. A user interface system for providing patient medical parameter data for trend indicative display covering a time period comprising user selectable acquisition time intervals, comprising:
    an acquisition processor for acquiring, from a patient monitoring device, data representing a patient parameter comprising a plurality of data values at a corresponding plurality of different times within multiple user selectable patient parameter acquisition intervals of a time period; and
    a generator for generating data representing a first image showing a trend indicative display of said patient parameter covering a time period comprising user selectable acquisition time intervals and including a first number of data points in an individual acquisition time interval, said first number of data points representing a value occuring at a time closest to a centre time of said individual acquisition time interval and for,
        generating data representing an image widow comprising an expansion of said individual acquisition time interval and including a second number of data points greater than said first number, in response to user command; and updating said individual acquisition time interval of said first image with at least one data point selected from said expanded individual acquisition time interval window to replace said first number of data points, in response to user command.

2. A user interface system according to claim 1, including a data processor supporting user editing of values of said second number of data points.

3. A user interface system according to claim 1, wherein said first number of data points is a single data point and said second number of data points is a single data point.

4. A user interface system according to claim 1, wherein said image window comprising an expansion of said individual acquisition time interval comprises a second time interval smaller than said individual acquisition time interval.

5. A user interface system according to claim 4, wherein said second time interval is movable within said individual acquisition time interval in response to a user navigation command.

6. A user interface system according to claim 1, wherein said second number of data points comprise raw data acquired by said acquisition processor.

7. A user interface system according to claim 1, wherein said second number of data points comprise one or more user selected data points acquired by said acquisition processor.

8. A user interface system according to claim 7, wherein said first number of data points comprise one or more points and including
a data processor for selecting said first number of data points to represent said selected individual acquisition time interval and supporting replacement of said selected one or more points by user selected data points acquired by said acquisition processor.

9. A user interface system according to claim 1, wherein said generator generates data representing an annotation associated with said individual acquisition time interval for incorporation in said first image in response to user command.

10. A user interface system according to claim 1, wherein said generator generates data representing an image window comprising an expansion of said multiple user selectable patient parameter acquisition intervals of a time period.

11. A user interface system according to claim 1, wherein said patient parameter comprises at least one of, (a) a blood pressure parameter, (b) a ventilation parameter, (c) a vital sign parameter, (d) a blood oxygen concentration representative parameter, (e) an infusion pump parameter associated with fluid delivery.

12. A user interface system for providing patient medical parameter data for trend indicative display covering a time period comprising user selectable acquisition time intervals, comprising:
an acquisition processor for acquiring, from a patient monitoring device, data representing a patient parameter comprising a plurality of data values at a corresponding plurality of different times within multiple user selectable patient parameter acquisition intervals of a time period; and
a generator for generating data representing a first image showing a trend indicative display of said patient parameter covering a time period comprising user selectable acquisition time intervals and, in response to user selection of an individual acquisition time interval, said patient parameter representing a value occurring at a time closest to a centre time of said individual acquisition time interval, for,
highlighting an acquisition interval and generating an image element enabling user initiation of, (a) generation of data representing an image window comprising an expansion of said individual acquisition time interval and (b) generation of data representing an annotation associated with said individual acquisition time interval for incorporation in said first image.

13. A user interface system according to claim 12, wherein said selected individual acquisition time interval includes a first number of data points, and including
a data processor supporting user editing of values of said first number of data points.

14. A user interface system according to claim 13, wherein said generator generates an image element enabling user initiation of at least one of, (a) acceptance and (b) cancellation of edited values of said first number of data points.

15. A user interface system according to claim 13, wherein said first number of data points comprise one or more points selected by said system to represent said selected individual acquisition time interval, and
said data processor supports replacement of said selected one or more points by user selected values of data acquired by said acquisition processor.

16. A user interface system for providing patient medical parameter data for trend indicative display covering a time period comprising user selectable acquisition time intervals, comprising:
an acquisition processor for acquiring, from a patient monitoring device, data representing a patient parameter comprising a plurality of data values at a corresponding plurality of different times within multiple user selectable patient parameter acquisition intervals of a time period; and
a generator for generating data representing a first image showing a trend indicative display of said patient parameter covering a time period comprising user selectable acquisition time intervals;
a filter for automatically selecting one or more data points, derived from said patient parameter data acquired by said acquisition processor, for display in association with an individual acquisition time interval, said one or more data points representing a value occurring at a time closest to a centre time of said individual acquisition time interval; and
a data processor for replacing values of said automatically selected one or more data points acquired by said acquisition processor with user selected values of data, in response to user command.

17. A method for processing patient medical parameter data for trend indicative display covering a time period comprising user selectable acquisition time intervals, comprising the steps of:
acquiring, from a patient monitoring device, data representing a patient parameter comprising a plurality of data values at a corresponding plurality of different times within multiple user selectable patient parameter acquisition intervals of a time period;
initiating generation of data representing a first image showing a trend indicative display of said patient parameter covering a time period comprising user selectable acquisition time intervals and including a first number of data points in an individual acquisition time interval, said first number of data points representing a value occurring at a time closest to a centre time of said individual acquisition time interval;

initiating generation of data representing an image window comprising an expansion of said individual acquisition time interval and including a second number of data points greater than said first number, in response to user command; and updating said individual acquisition time interval of said first image with at least one data point selected from said expanded individual acquisition time interval window to replace said first number of data points, in response to user command.

18. A method for processing patient medical parameter data for trend indicative display covering a time period comprising user selectable acquisition time intervals, comprising the steps of:

acquiring, from a patient monitoring device, data representing a patient parameter comprising a plurality of data values at a corresponding plurality of different times within multiple user selectable patient parameter acquisition intervals of a time period;

initiating generation of data representing a first image showing a trend indicative display of said patient parameter covering a time period comprising user selectable acquisition time intervals and including a first number of data points in an individual acquisition time intervals, said first number of data points representing a value occurring at a time closest to a centre time of said individual acquisition time interval; and in response to user selection of an individual acquisition time interval, generating an image element enabling user initiation of at least one of, (a) generation of data representing an image window comprising an expansion of said individual acquisition time interval and (b) generation of data representing an annotation associated with said individual acquisition time interval for incorporation in said first image.

19. A method for processing patient medical parameter data for trend indicative display covering a time period comprising user selectable acquisition time intervals, comprising the steps of:

acquiring, from a patient monitoring device, data representing a patient parameter comprising a plurality of data values at a corresponding plurality of different times within multiple user selectable patient parameter acquisition intervals of a time period; and initiating generation of data representing a first image showing a trend indicative display of said patient parameter covering a time period comprising user selectable acquisition time intervals;

automatically selecting one or more data points, derived from said patient parameter data acquired by said acquisition processor, for display in association with an individual acquisition time interval, said one or more data points representing a value occurring at a time closest to a centre time of said individual acquisition time interval and replacing values of said automatically selected one or more data points acquired by said acquisition processor with user selected values of data, in response to user command.

* * * * *